June 30, 1970 F. W. ANDERSON Plant Pat. 2,975
PEAR TREE
Filed July 29, 1968
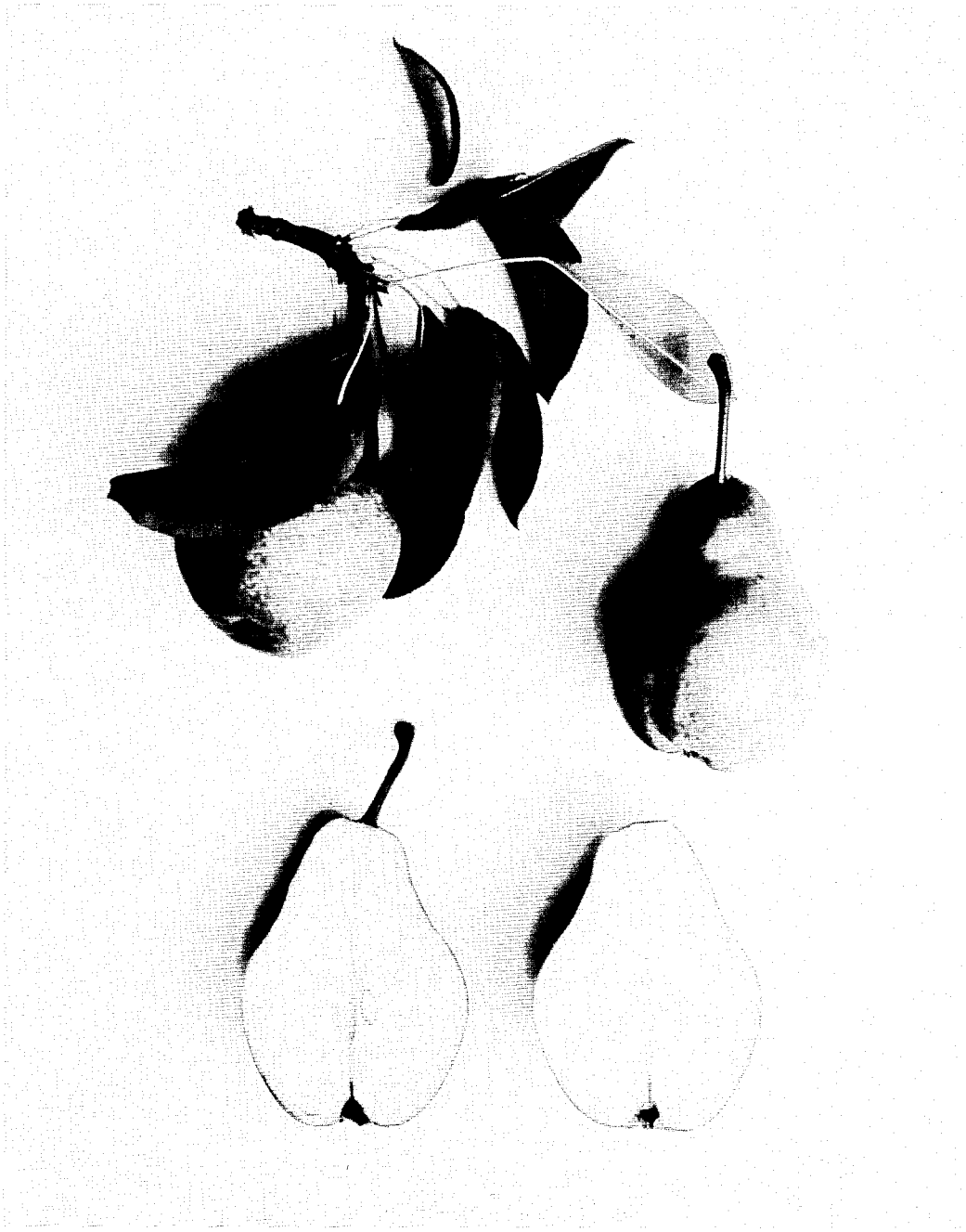
INVENTOR
Frederic W. Anderson
BY
Webster & Webster
ATTORNEYS United States Patent Office Plant Pat. 2,975
Patented June 30, 1970

2,975
PEAR TREE

Frederic W. Anderson, Merced, Calif., assignor to Fowler Nurseries, Inc., Newcastle, Calif., a corporation of California Filed July 29, 1968, Ser. No. 748,572
Int. Cl. A01l 5/03
U.S. Cl. Plt.—36 1 Claim

ABSTRACT OF THE DISCLOSURE

A medium size, vigorous, rapid growing variety of pear tree which is tall and spreading and a regular and productive bearer of large to medium size fruit which turns from a light yellow-green when hard ripe to predominantly yellow when full ripe.

BACKGROUND OF THE VARIETY

Over a substantial number of years I have engaged in an extensive and continuing plant breeding program at my experimental nursery and orchard located near Le Grand, Merced County, Calif.; one purpose of such program being to provide improved varieties of fruit trees. The present variety of pear tree resulted from my endeavors in the conduct of such plant breeding program.

ORIGIN OF THE VARIETY

The herein disclosed new and distinct variety of pear tree was originated by me in my experimental orchard located as aforesaid in the following manner:

I obtained a substantial number of seeds of a Bartlett (unpatented) pear tree whose flowers had been fertilized by pollen from a Rose of July (unpatented) pear tree, and such seeds were planted and the resultant seedlings maintained under careful and continuing observation. When such seedlings bore fruit, one—and which is the instant variety—evidenced novel and commercially desirable characteristics and was, therefore, selected by me for asexual reproduction, preparatory to introduction to the trade.

ASEXUAL REPRODUCTION OF THE VARIETY

After its origination, as above, I asexually reproduced the variety by grafting on a mature pear tree (unnamed) in my said experimental orchard, and—in maturity—such reproductions all ran true to the parent tree in every respect.

SUMMARY OF THE VARIETY

The herein claimed new and distinct variety of pear tree is of medium size, vigorous, rapid growing, tall and spreading, and a regular and productive bearer of large to medium size fruit which turns from a yellow-green when hard ripe to predominantly yellow when full ripe; the variety, in both tree and fruit, generally resembling the Bartlett, but is distinctive in comparison by fruit which ripens about one week to ten days earlier.

The herein claimed new and distinct variety of pear tree is also characterized, in comparison to the Bartlett, by fruit which achieves a higher soluble solids content while the flesh remains firm, and flesh which softens more gradually and uniformly; these characteristics, together with the early ripening period, give promise that the fruit will be very satisfactory for long distance fresh shipment, and processing purposes, as well as the local fresh fruit market.

BRIEF DESCRIPTION OF THE DRAWING

The drawing is an illustration, by photographic reproduction in color, of the fruit and leaves; one fruit being cut in half with the halves disposed to expose the flesh.

DESCRIPTION OF THE VARIETY

The botanical details of this new and distinct variety of pear tree—with color definitions (except those in common color terms) referenced to Maerz and Paul Dictionary of Color—are as follows:

Tree:
- *Size.*—Medium.
- *Vigor.*—Vigorous.
- *Growth.*—Tall; spreading; rapid.
- *Production.*—Productive.
- *Bearing.*—Regular bearer.

Trunk:
- *Size.*—Medium.
- *Texture.*—Medium.

Branches:
- *Size.*—Medium.
- *Color.*—Brown.
- *Lenticels.*—Number—medium. Size—medium.

Leaves:
- *Size.*—Medium—both length and width. Average length—3½". Average width—1¾".
- *Form.*—Ovate; taper pointed.
- *Thickness.*—Medium.
- *Texture.*—Smooth.
- *Margin.*—Finely serrate.
- *Petiole.*—Medium length—average 1½". Medium thickness.
- *Color.*—Top side—Dark Green (24–J–10). Under side—Lighter Green (22–I–6).

Flowers:
- *Blooming period.*—Early to medium—2 or 3 days before Bartlett.
- *Size.*—Large.
- *Fertility.*—Self-fertile, as well as interfertile with Bartlett.

Fruit:
- *Maturity when described.*—Hard ripe.
- *Ripening period.*—About 1 week or 10 days earlier than Bartlett.
- *Retention.*—Hangs well.
- *Size.*—Large to medium. Average length (well grown specimen)—4". Average width (well grown specimen)—2⅝". Uniform.
- *Form.*—Obovate; pyriform, resembling Bartlett; symmetrical; uniform.
- *Stem.*—Medium length—average 1½". Medium thickness.
- *Cavity.*—Obtuse; shallow; lipped; russeted.
- *Calyx.*—Closed; small. Lobes—medium length; narrow; acute.
- *Basin.*—Shallow; medium width; obtuse; furrowed.

Skin:
- *Thickness.*—Medium.
- *Texture.*—Smooth.
- *Color.*—Light Yellow-Green (20-L–6) when hard ripe shading to predominantly yellow when full ripe, often with slight blush (red) on sunny side, and width small Russet (14–K–9) area around base of stem. Dots—Green (21–L–8) when fruit hard ripe.

Flesh:
- *Color.*—White (18–B–1).
- *Texture.*—Fine; crisp; tender; juicy.
- *Flavor.*—Subacid; sprightly.
- *Eating quality.*—Very good.
- *Core.*—Medium size; closed.
- *Core lines.*—Clasping.
- *Calyx tube.*—Length — Long. Width — medium. Form—funnel-shaped.
- *Seed.*—Medium size; plump; acute. Color—Cornsilk (10–G–3).

Use: Dessert; local and long distance market; processing.
Keeping quality: Good.
Shipping quality: Good.

The pear tree and its fruit herein described may vary in slight detail due to climatic and soil conditions under which the variety may be grown; the present description being of the variety as grown in the Central Valley of California.

I claim:

1. A new and distinct variety of pear tree, substantially as illustrated and described, which is of medium size, vigorous, rapid growing, tall and spreading, in bloom two to three days before Bartlett with flowers both interfertile therewith, as well as self-fertile, and a regular and productive bearer of large to medium size fruit which turns from light yellow-green when hard ripe to a predominantly yellow when full ripe; the tree and its fruit generally resembling the Bartlett but distinctive, in comparison, by fruit which ripens about one week to ten days earlier, achieves a higher soluble solids content while the flesh remains firm, and which flesh softens more gradually and uniformly.

No references cited.

ROBERT E. BAGWILL, Primary Examiner